United States Patent
Hamada et al.

(10) Patent No.: US 8,126,243 B2
(45) Date of Patent: Feb. 28, 2012

(54) IMAGE PROCESSING METHOD, IMAGE PROCESSING PROGRAM, AND IMAGE PROCESSING DEVICE

(75) Inventors: Kazuo Hamada, Nishinomiya (JP); Kazuhiro Nishikawa, Nishinomiya (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 937 days.

(21) Appl. No.: 12/064,430

(22) PCT Filed: Feb. 21, 2006

(86) PCT No.: PCT/JP2006/316147
§ 371 (c)(1),
(2), (4) Date: Feb. 21, 2008

(87) PCT Pub. No.: WO2007/023723
PCT Pub. Date: Mar. 1, 2007

(65) Prior Publication Data
US 2009/0148019 A1 Jun. 11, 2009

(30) Foreign Application Priority Data
Aug. 23, 2005 (JP) ................................ 2005-241624

(51) Int. Cl.
*G06K 9/00* (2006.01)
(52) U.S. Cl. ........................................ 382/131; 382/294
(58) Field of Classification Search .......... 382/128–132, 382/294–298; 378/98.11, 98.12
See application file for complete search history.

(56) References Cited

U.S. PATENT DOCUMENTS
6,728,424 B1 4/2004 Zhu et al.
6,904,163 B1 6/2005 Fujimura et al.

FOREIGN PATENT DOCUMENTS
JP 2000-40145 A 2/2000
JP 2004-508856 A 3/2004

OTHER PUBLICATIONS

"Optimization Algorithms", Tomoharu Nagao, first edition, Shokodo Co., Ltd, 2000, p. 38-p. 85.
"A Fully Automatic Multimodality Image Registration Algorithm", Babak A. Ardekani et al., Journal of Computer Assisted Tomography (USA), Apr. 19, 1995, p. 615-p. 623.
"Multimodality Image Registration by Maximization of Mutual Information", F. Maes et al., IEEE Transactions on Medical Imaging, vol. 16, No. 2 (USA), Apr. 1997, p187-1p98.
International Search Report by JPO, Mailed Nov. 14, 2006.

(Continued)

*Primary Examiner* — Courtney Thomas
(74) *Attorney, Agent, or Firm* — Greenlee Sullivan P.C.

(57) ABSTRACT

An image processing method is provided as one for creating a fused image automatically and with high overlapping accuracy.
An image processing method according to an embodiment of the present invention includes (a) a voxel normalization step of equalizing voxel sizes and numbers of voxels in respective effective fields of view of a first 3D image based on a plurality of first tomographic images obtained from an arbitrary part of a subject and a second 3D image based on a plurality of second tomographic images obtained from the same part, thereby creating a first normalized 3D image corresponding to the first 3D image and a second normalized 3D image corresponding to the second 3D image; and (b) a fused image creation step of creating a fused image, using the first normalized 3D image and the second normalized 3D image.

15 Claims, 16 Drawing Sheets

OTHER PUBLICATIONS

English Translation of the International Preliminary Report on Patentability mailed on Mar. 6, 2008 for International Application No. PCT/JP2006/316147.

Studholme C et al. "An overlap invariant entropy measure of 30 medical image alignment"; (1999) *Pattern Recognition*, Elsevier GB 32(1) 71-86.

Pluim PW et al. "Mutual-information-based registration of medical images: a survey"; (2003) *IEEE Transations on Medical Imaging*, 22(8) 986-1004.

Bottger T et al. "Registration of CT and MRI volume data of the liver"; (2003) *International congress series*, 1256:118-123.

Fei, B et al. "Automatic MR volume registration and its evaluation for the pelvis and prostate"; (2002) *Physics in Medicine and Biolgl*, 47:823-838.

EP Supplementary Search report for related EP application 06 79 6504 (Jul. 13, 2011).

"Dr. View/LINUX User's Manual (ver.3)"; (Jan. 2004) AJG (Asahi Kasei Joho System) Inc. p. 466-470.

IMAGE PROCESSING METHOD, IMAGE PROCESSING PROGRAM, AND IMAGE PROCESSING DEVICE

CROSS-REFERENCE TO RELATED APPLICATIONS

This application is a United States national stage application under 35 U.S.C. §371 of International Application No. PCT/JP2006/316147, filed Aug. 17, 2006, which claims benefit of Japan Patent Application No. P2005-241624 filed Aug. 23, 2005; both of which are hereby incorporated by reference in their entireties to the extent not inconsistent with the disclosure herein.

TECHNICAL FIELD

The present invention relates to an image processing method, image processing program, and image processing apparatus for creating a fused image by overlapping a pair of three-dimensional (3D) tomographic images.

BACKGROUND ART

The diagnostic imaging which is implemented using images including single photon emission computed tomography (hereinafter referred to as "SPECT") images, positron emission tomography (hereinafter referred to as "PET") images, magnetic resonance imaging (hereinafter referred to as "MRI") images, and x-ray computed tomography (hereinafter referred to as "CT") images can obtain information about a lesioned part existing in a body of a subject in a nondestructive manner. Therefore, the diagnostic imaging is essential to the current medical diagnosis.

Various studies have been conducted heretofore on the diagnostic imaging technology and in recent years the technology of imaging which obtain not only morphologic information of a part in a living body but also functional information of the living body has been developed and is clinically applied. For example, the functional magnetic resonance imaging tomography (hereinafter referred to as "fMRI") for imaging a local change in blood flow in a brain by using the nuclear magnetic resonance, and nuclear medicine such as SPECT and PET were developed and is clinically applied.

Such functional images are images obtained by imaging a functional change in a living body and a lesion. Therefore, the functional images have the advantage of high specificity for detection of a lesioned part. On the other hand, the functional images also have the disadvantage of lacking anatomical position information of the lesioned part.

A fused image is used for the purpose of compensating for the disadvantage of the functional images. The fused image is an image obtained by overlapping a functional image and a morphologic image. This fused image permits us to confirm an anatomical position of the lesioned part detected in the functional image, on the morphologic image. Therefore, the fused image is useful for definite diagnosis, determination of therapeutic strategy, and so on.

The fused image can be created from images originating in such different modalities, i.e., images acquired by different devices, and also from images originating in the same modality. For example, when the fused image is one based on a plurality of nuclear medicine images obtained by executing the same inspection multiple times, we can obtain, for instance, a change in value at the same part, different pieces of blood flow information from the same part, or a receptor distribution.

Reflecting the increase in such needs for the fused image, a variety of methods have been proposed and developed heretofore for automatically creating the fused image. For example, the Automatic Multimodality Image Registration method (hereinafter referred to as the AMIR method) (cf. Non-patent Document 1), the AC-PC line alignment method (cf. Non-patent Document 2), the mutual information maximization method (cf. Non-patent Document 3), and others have been developed and put to practical use.

Non-patent Document 1: Babak A. Ardekani et al., "A Fully Automatic Multimodality Image Registration Algorithm," Journal of Computer Assisted Tomography, (USA), 1995, 19, 4, p 615-623

Non-patent Document 2: "Dr. View/LINUX User Manual (ver. 3)," AJS (Asahikasei Joho System) Inc., p. 466-470

Non-patent Document 3: F. Maes et al., "Multimodality Image Registration by Maximization of Mutual Information," IEEE Transactions on Medical Imaging, (USA), 1997, 16, 2, p 187-198

DISCLOSURE OF THE INVENTION

Problem to be Solved by the Invention

As described above, the fused image is very useful in the field of diagnostic imaging and many fused image creating methods have been developed heretofore and put to practical use.

The AMIR method is a method of dividing images subjected to extraction of contour, into segments and finding a condition to minimize an evaluation function, thereby creating the fused image. This method is effective for images that can be divided into segments, but is not suitable for images that are vaguely-outlined and hard to be divided into segments, like images of a target of soft tissue.

The AC-PC line alignment method is a method of creating the fused image by overlapping the AC-PC lines determined in the mid-sagittal plane. This method allows the fused image to be readily created once the AC-PC lines are determined in the respective images to be subjected to overlapping. However, this method is based on the premise that the images are created in the mid-sagittal plane and that the AC-PC lines are manually determined, and thus this method has the disadvantage that the operation of determining the AC-PC lines per se is complicated. This method cannot be applied to images of targets except for the head.

On the other hand, the mutual information maximization method is a method of performing position alignment using the amount of information of each image. Namely, this method does not require such operation as the division into segments or the determination of the AC-PC line. Therefore, the mutual information maximization method can be said to be one of the most useful position alignment methods at present.

However, the overlapping accuracy is not always high for the fused image automatically created by the mutual information maximization method and it is often the case that manual readjustment is needed. This problem often arises, particularly, with the fused image resulting from a combination of images originating in different modalities, for example, like the fused image using SPECT images and CT images.

An object of the present invention is therefore to provide an image processing method, image processing program, and image processing apparatus for creating the fused image automatically and with high overlapping accuracy.

Means for Solving the Problem

The Inventor conducted elaborate research and came to have the expertise for creating the fused image with good accuracy. Namely, the Inventor found that the accurate fused image could be created by equalizing voxel sizes and numbers of voxels of a pair of 3D images and thereafter obtaining corresponding positions in the pair of 3D images. In the conventional technology, the pair of 3D images with different voxel sizes and numbers of voxels was fed directly to the calculation process for deriving the corresponding positions between them. This is because the mutual information maximization method or the like introduces a rescaling process for deriving the corresponding positions using a pair of 3D images with different voxel sizes and numbers of voxels, and conventionally, the necessity for equalizing the voxel sizes and numbers of voxels of the pair of respective 3D images was not recognized.

An image processing method according to an aspect of the present invention based on the above-described expertise comprises: (a) a voxel normalization step of equalizing voxel sizes and numbers of voxels in respective effective fields of view of a first 3D image based on a plurality of first tomographic images obtained from an arbitrary part of a subject and a second 3D image based on a plurality of second tomographic images obtained from the same part, thereby creating a first normalized 3D image corresponding to the first 3D image and a second normalized 3D image corresponding to the second 3D image; and (b) a fused image creation step of creating a fused image, using the first normalized 3D image and the second normalized 3D image.

The image processing method of the present invention may further comprise a voxel shape transformation step of transforming each voxel in a first 3D original image consisting of the plurality of first tomographic images or in a second 3D original image consisting of the plurality of second tomographic images, into a voxel of a cubic shape, thereby creating the first 3D image and the second 3D image.

An image processing program according to another aspect of the present invention is a program for letting a computer execute the above-described voxel normalization step and fused image creation step. The image processing program of the present invention may let the computer further execute the aforementioned voxel shape transformation step.

An image processing apparatus according to still another aspect of the present invention comprises: (a) voxel normalizing means for equalizing voxel sizes and numbers of voxels in respective effective fields of view of a first 3D image based on a plurality of first tomographic images obtained from an arbitrary part of a subject and a second 3D image based on a plurality of second tomographic images obtained from the same part, thereby creating a first normalized 3D image corresponding to the first 3D image and a second normalized 3D image corresponding to the second 3D image; and (b) fused image creating means for creating a fused image, using the first normalized 3D image and the second normalized 3D image.

The image processing apparatus of the present invention may further comprise voxel shape transforming means for transforming each voxel in a first 3D original image consisting of the plurality of first tomographic images or in a second 3D original image consisting of the plurality of second tomographic images, into a voxel of a cubic shape, thereby creating the first 3D image and the second 3D image.

The first normalized 3D image and the second normalized 3D image are preferably created by a linear interpolation method. The first 3D image or the second 3D image are also preferably created by a linear interpolation method. The fused image may be created by the mutual information maximization method.

EFFECT OF THE INVENTION

The present invention provides the image processing method, image processing program, and image processing apparatus capable of creating the fused image automatically and with high overlapping accuracy.

DESCRIPTION OF REFERENCE SYMBOLS 10 image processing program; 11 main module; 12 3D original image acquisition module; 14 voxel shape transformation module; 16 voxel normalization module; 18 fused image creation module; 20 output module; 30 image processing apparatus; 32 3D original image acquiring unit; 34 voxel shape transforming unit; 36 voxel normalizing unit; 38 fused image creating unit; 40 output unit; 100 recording medium; 110 computer; 112 reading device; 114 working memory;

116 memory; 118 display unit; 120 mouse; 122 keyboard; 124 communication device; 126 CPU.

BEST MODE FOR CARRYING OUT THE INVENTION

Figure 1:
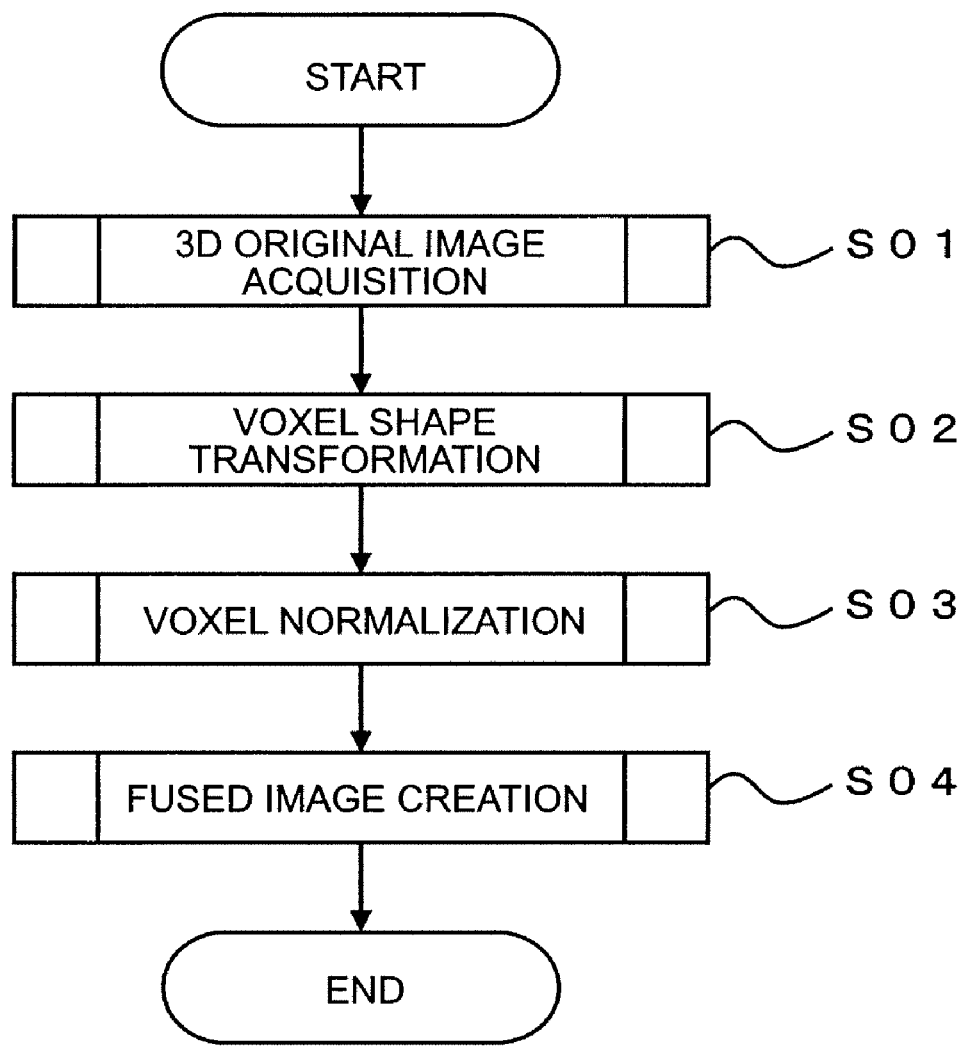
FIG. 1 is a flowchart of an image processing method according to an embodiment of the present invention.

An image processing method according to an embodiment of the present invention will be described below with reference to the drawings. FIG. 1 is a flowchart of the image processing method according to the embodiment of the present invention. The image processing method shown in FIG. 1 can be executed, for example, by supplying commands of respective steps described below, to a computer.

As shown in FIG. 1, this image processing method includes the first step of acquiring a first 3D original image and a second 3D original image for creating a fused image (step S01). The first 3D original image consists of first tomographic images in a plurality of sections obtained from an arbitrary part in a subject. Similarly, the second 3D original image consists of second tomographic images in a plurality of sections obtained from the same part.

It is assumed in the present embodiment that the first tomographic images and the second tomographic images are images acquired in different modalities. Specifically, the first tomographic images are assumed to be functional images, such as SPECT images and PET images, and the second tomographic images are assumed to be morphologic images, such as MRI images and CT images. The following will describe an example where the morphologic images are CT images and the functional images are SPECT images.

It is noted herein that the first tomographic images and the second tomographic images may be images acquired in the same modality. For example, the first tomographic images and the second tomographic images can also be PET images or SPECT images taken at different dates and times of imaging from the same part or with different radiopharmaceuticals administered, or MRI images taken under different imaging conditions.

The plurality of first tomographic images and the plurality of second tomographic images are tomographic images acquired from a plurality of sections approximately perpendicular to the body axis and consecutive in the direction of the body axis. Each of these images can be acquired by any one of the well-known methods. In the description hereinafter, a coordinate system is defined as follows on a front view of a body: a lateral direction is defined as an x-axis direction, a depth direction as a y-axis direction, and the body-axis direction as a z-axis direction.

The image data of each of the first 3D original image and the second 3D original image may be data stored in a computer-readable data format and can be, for example, data in the DICOM format. These pieces of image data are provided, for example, in a form stored in a computer-readable storage medium such as a compact disk. The storage medium storing the image data is put into a data reading device installed in a computer, whereby the computer retrieves the image data and becomes ready to perform the following image processing using these images. The data may be so arranged that it is directly acquired through a network, as a computer data signal superimposed on a carrier wave.

The image processing method of the present embodiment includes the next step of a voxel shape transformation step (step S02). In the first 3D original image and the second 3D original image, i.e., the 3D original images consisting of the plurality of tomographic images, each voxel can be of a rectangular parallelepiped shape extending in the z-axis direction. The voxel shape transformation step is to execute a process of transforming each voxel in the first 3D original image and the second 3D original image into a voxel of a cubic shape.

This step is not carried out if each voxel in the first 3D original image and the second 3D original image is of the cubic shape, and then the first 3D original image is used as a first 3D image and the second 3D original image as a second 3D image. If the voxels in one of the first 3D original image and the second 3D original image are of the rectangular parallelepiped shape, the voxels in the one 3D original image are transformed into voxels of the cubic shape.

The voxel shape transformation step (step S02) will be described below in more detail. The process of this step is to adjust the pixel size in the body-axis direction, for example, according to a well-known linear interpolation method such as the bilinear method or the bicubic method.

Figure 2:
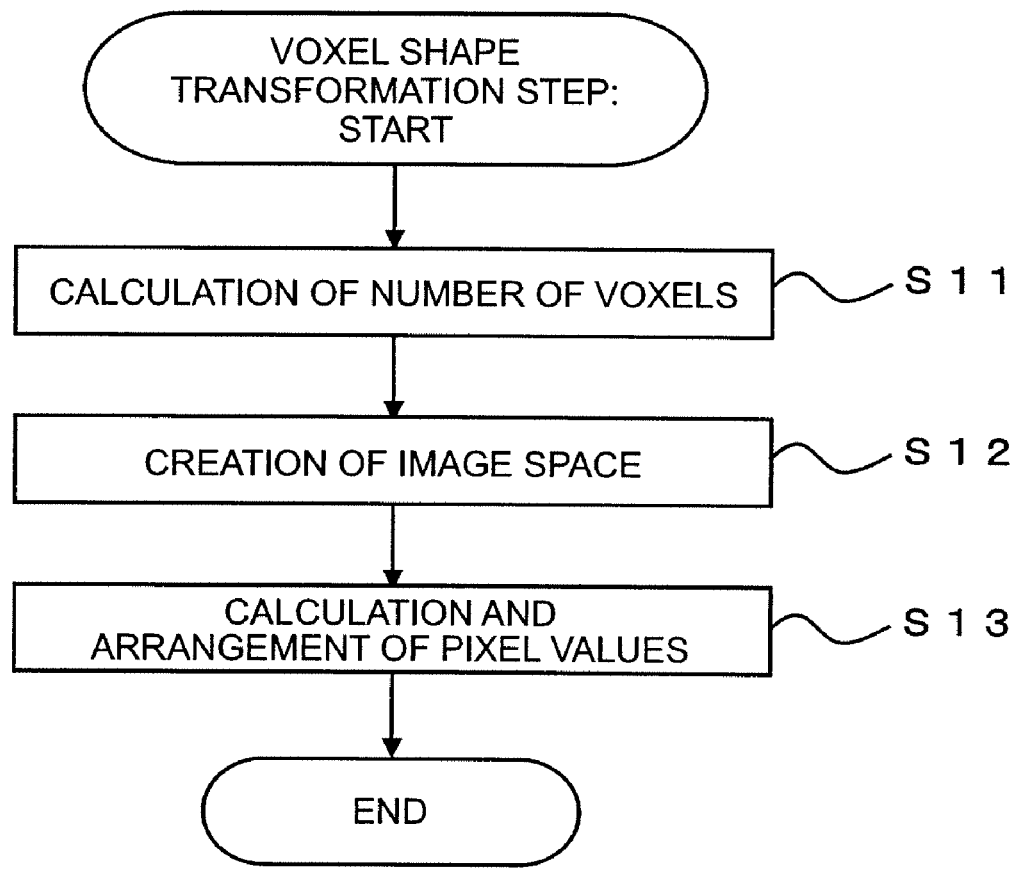
FIG. 2 is a flowchart showing an example of processing in a voxel shape transformation step shown in FIG. 1.

This step will be described below using an example of linear interpolation by the bilinear method. FIG. 2 is a flowchart showing an example of processing in the voxel shape transformation step shown in FIG. 1. The processing based on the bilinear method is adopted in the voxel shape transformation step shown in FIG. 2. In this voxel shape transformation step, processes of steps S11-S13 described bellow are applied to both of the first 3D original image and the second 3D original image to generate the first 3D image and the second 3D image. For simplicity of description, the first 3D original image and the second 3D original image will be represented hereinafter by "3D original image." The first 3D image and the second 3D image created by the voxel shape transformation will be represented by "3D image."

As shown in FIG. 2, this voxel shape transformation step includes the first step to calculate the number of voxels in the z-axis direction after the voxel shape transformation in an effective field of view, in order to adjust only the number of voxels in the z-axis direction (step S11).

Specifically, the calculation according to Eq (1) below is carried out to calculate the number of voxels in the z-axis direction.

[Mathematical Expression 1]

$$M_{z2} = \frac{FOV_z}{P_1} \quad (1)$$

In Eq (1), $M_{z2}$ is the number of voxels in the z-axis direction after the voxel shape transformation, $FOV_z$ the effective field of view in the z-axis direction, and $P_1$ a length of one side in the x-axis and y-axis directions of each voxel. In this manner, the number in the z-axis direction of voxels of the cubic shape with the length of one side of $P_1$ is calculated.

The next step is to create a new image space for the 3D image after the voxel shape transformation, on a memory (step S12). This image space is a space for storing pixel values of respective voxels the number of which is equal to a product of the number of voxels in the x-axis direction and the number of voxels in the y-axis direction in the 3D original image, and $M_{z2}$.

The next step is to create a new 3D image by assigning pixel values to the respective voxels in the image space prepared in step S12 (step S13). In this step, the 3D image is created by using coronal images or sagittal images in the 3D original image and applying the linear interpolation by the bilinear method in the z-axis direction. The following will describe an example where the linear interpolation is performed using coronal images.

In step S13, pixel value g(x,z) at point (x,z) is calculated according to Eq (2) below from pixel values of 3D original image f of four respective grid points $(j_1, k_1)$, $(j_1+1, k_1)$, $(j_1, k_1+1)$, and $(j_1+1, k_1+1)$ around and near a center point (x,z) of an arbitrary voxel in the 3D image g after the voxel shape transformation.

[Mathematical Expression 2]

$$g(x,z) = (1-r_1)\cdot(1-s_1)\cdot f(j_1,k_1) + r_1\cdot(1-s_1)\cdot f(j_1+1,k_1) + \qquad (2)$$
$$(1-r_1)\cdot s_1 \cdot f(j_1, k_1+1) + r_1 \cdot s_1 \cdot f(j_1+1, k_1+1)$$

In this equation, $f(j_1, k_1)$, $f(j_1+1, k_1)$, $f(j_1, k_1+1)$, and $f(j_1+1, k_1+1)$ are pixel values (density values of pixels) at the respective grid points $(j_1, k_1)$, $(j_1+1, k_1)$, $(j_1, k_1+1)$, and $(j_1+1, k_1+1)$ of a coronal image in the 3D original image surrounding the point (x,z), $j_1=[x]$, $r_1=x-j_1$, $k_1=[z]$, and $s_1=z-k_1$. This operation is sequentially carried out for all the voxels in all the coronal images thereby to form the new image or the 3D image g in the transformed voxel shape of the cubic shape, thus completing the voxel shape transformation processing.

Returning to FIG. 1, the image processing method of the present embodiment next involves executing a voxel normalization step (step S03). This voxel normalization step is to execute a process of equalizing the voxel sizes and the numbers of voxels in the respective effective fields of view of the first 3D image and the second 3D image.

In the most preferred form, the voxel normalization step is to implement such a transformation that the voxel size and the number of voxels in the image with the smaller effective field of view are changed so as to equal the voxel size and the number of voxels in the image with the larger effective field of view.

For example, in a case where the effective field of view of the first 3D image is smaller than the effective field of view of the second 3D image, the voxel size and the number of voxels in the first 3D image are matched with the voxel size and the number of voxels in the second 3D image. The Null code (or value 0) is assigned to the region other than the effective field in the first 3D image.

Figure 3:
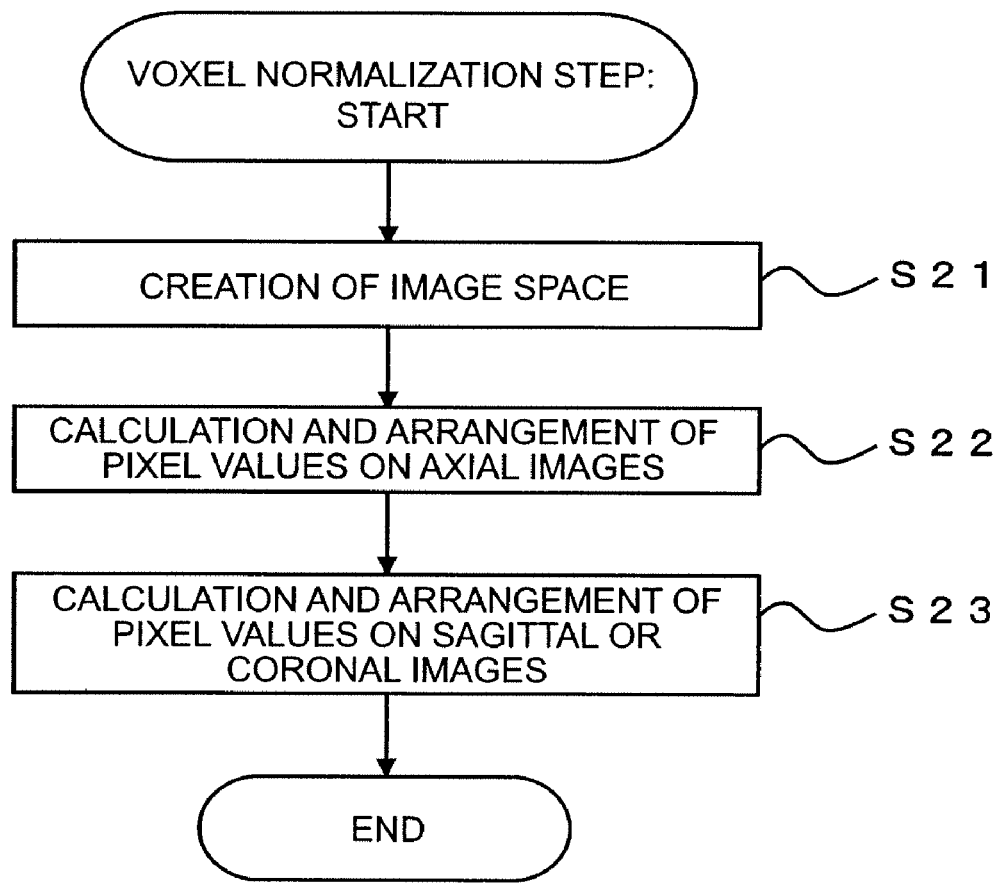
FIG. 3 is a flowchart showing an example of processing in a voxel normalization step shown in FIG. 1.

In this voxel normalization step, it is also possible to adopt the well-known linear interpolation process such as the bilinear method or the bicubic method. FIG. 3 is a flowchart showing an example of processing in the voxel normalization step shown in FIG. 1. Assuming that the second 3D image has the effective field of view larger than the first 3D image, the voxel normalization step based on the bilinear method will be described below with reference to FIG. 3.

In the voxel size and other normalization step, as shown in FIG. 3, the first process is to prepare a 3D image space having the same voxel size and number of voxels as those of the second 3D image, on a memory of a computer (step S21).

The next process is to create a first 3D normalized image by assigning pixel values obtained by linear interpolation from the first 3D image, to the respective voxels in the image space. In the present embodiment the second 3D image is used as a second 3D normalized image as it is.

More specifically, first, axial images of the first 3D image are used to perform the linear interpolation by the bilinear method to calculate provisional pixel values, and the provisional pixel values are assigned to the respective voxels in the image space (step S22). The interpolation process of step S22 will be referred to hereinafter as "primary interpolation process."

Specifically, in the primary interpolation process, xy coordinates are set on each axial image. Then grid points are supposed on the image space, and pixel value $h_1(x,y)$ at point (x,y) is calculated according to Eq (3) below from pixel values in the first 3D image g of four respective grid points $(j_2, k_2)$, $(j_2+1, k_2)$, $(j_2, k_2+1)$, and $(j_2+1, k_2++1)$ around a point (x,y) in a 3D image $h_1$ after the primary interpolation process.

[Mathematical Expression 3]

$$h_1(x,y) = (1-r_2)\cdot(1-s_2)\cdot h1(j_2,k_2) + r_2\cdot(1-s_2)\cdot g(j_2+1,k_2) + \qquad (3)$$
$$(1-r_2)\cdot s_2 \cdot g(j_2, k_2+1) + r_2 \cdot s_2 \cdot g(j_2+1, k_2+1)$$

In this equation, $g(j_2, k_2)$, $g(j_2+1, k_2)$, $g(j_2, k_2+1)$, and $g(j_2+1, k_2+1)$ are pixel values in the first 3D image g at the respective grid points $(j_2, k_2)$, $(j_2, k_2)$, $(j_2, k_2+1)$, and $(j_2+1, k_2+1)$ around the point (x,y), $j_2=[x]$, $r_2=x-j_2$, $k_2=[y]$, and $s_2=y-k_2$. This operation is sequentially carried out for all the voxels in all the axial images, and the resultant pixel values are assigned to the respective voxels, thereby completing the primary interpolation process.

Thereafter, a similar interpolation process is carried out with sagittal images or coronal images (step S23). The process of step S23 will be referred to hereinafter as a secondary interpolation process. The following will describe the secondary interpolation process using an example where the interpolation process is carried out with the coronal images.

In the secondary interpolation process, first, xz coordinates are set on each coronal image. Then grid points are supposed on the coordinates and pixel value $h_2(x,z)$ at point (x,z) is calculated according to Eq (4) below from four pixel values in the 3D image $h_1$ subjected to the primary interpolation process, which are pixel values at four respective grid points $(j_3, k_3)$, $(j_3+1, k_3)$, $(j_3, k_3+1)$, and $(j_3+1, k_3+1)$ around a center point (x,z) of an arbitrary voxel.

[Mathematical Expression 4]

$$h_2(x,y) = (1-r_3)\cdot(1-s_3)\cdot h1(j_3,k_3) + r_3\cdot(1-s_3)\cdot g(j_3+1,k_3) + \qquad (4)$$
$$(1-r_3)\cdot s_3 \cdot g(j_3, k_3+1) + r_3 \cdot s_3 \cdot g(j_3+1, k_3+1)$$

In this equation, $h_1(j_3, k_3)$, $h_1(j_3+1, k_3)$, $h_1(j_3, k_3+1)$, and $h_1(j_3+1, k_3+1)$ are pixel values at the respective grid points $(j_3, k_3)$, $(j_3+1, k_3)$, $(j_3, k_3+1)$, and $(j_3+1, k_3+1)$ around the point (x,z), $j_3=[x]$, $r_3=x-j_3$, $k_3=[z]$, and $s_3=z-k_3$. This operation is sequentially carried out for all the voxels and the resultant pixel values are assigned to the respective voxels, thereby obtaining the first normalized 3D image $h_2$. This completes the secondary interpolation process and thereby completes the voxel size and other normalization process.

If the first 3D image has the effective field of view larger than the second 3D image, the same processes as the above-described steps S21-S23 are carried out for the second 3D image. The voxel normalization step may also be configured to perform a process of matching the number of voxels in the image with the larger effective field of view with that in the image with the smaller effective field of view. For example, in a case where the effective field of view of the first 3D image is smaller than the effective field of view of the second 3D image, the voxel normalization step can be configured to execute a process of matching the voxel size and the number of voxels in the second 3D image with the voxel size and the number of voxels in the first 3D image. In this case, it is necessary to transform the second 3D image so that the part in the effective field of view of the second 3D image after the transformation becomes a part substantially equal to the part in the effective field of view of the first 3D image. Specifically, a target part, i.e., a 3D region of interest is selected in the second 3D image by means of an external input means such as a mouse, and the linear interpolation process is carried out for the selected target part, to implement the normalization processing, whereby a fused image in the target part can be created at high speed.

Reference is made again to FIG. 1. In the image processing method of the present embodiment, the voxel normalization step is followed by a fused image creation step (step S04). This fused image creation step is to execute a overlapping process of the first normalized 3D image and the second normalized 3D image, thereby creating a fused image.

Figure 4:
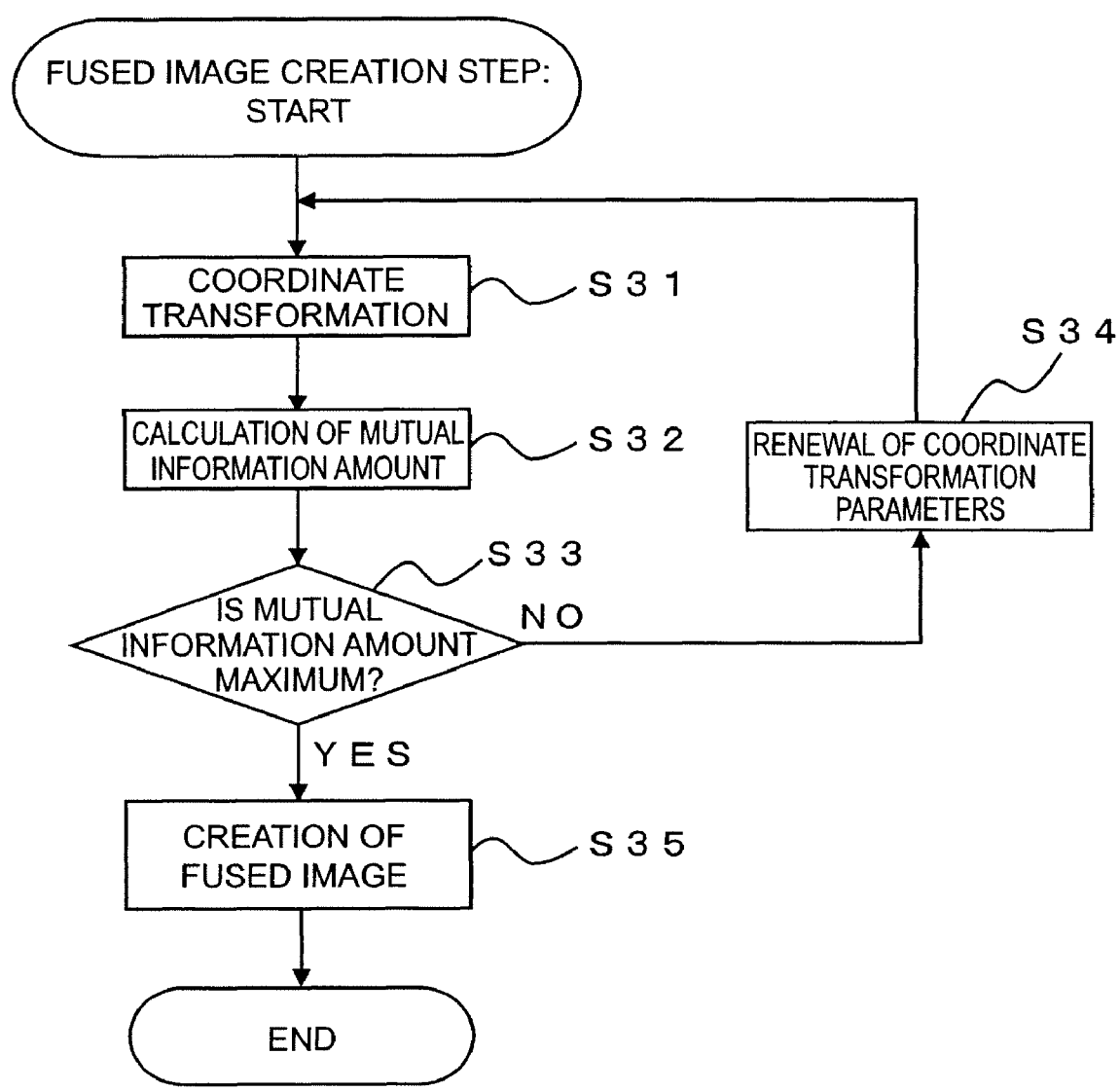
FIG. 4 is a flowchart showing an example of processing in a fused image creation step shown in FIG. 1.

This overlapping process is carried out using the mutual information maximization method (Maes F. et al., IEEE Trans. Med. Imaging, (1997), 16(2), p. 187-198). The following will describe the overlapping process of images in the mutual information maximization method. The mutual information maximization method is a method of creating overlapped images under a condition to maximize the amount of mutual information between images. FIG. 4 is a flowchart showing an example of processing in the fused image creation step shown in FIG. 1.

Specifically, the mutual information maximization method, as shown in FIG. 4, includes the first process of performing a coordinate transformation of the first normalized 3D image using given coordinate transformation parameters (step S31). The coordinate transformation parameters used herein are a total of six parameters, parameters (Tx, Ty, Tz) for translation of image and parameters ($\theta x$, $\theta y$, $\theta z$) for rotation of image. The initial values of the coordinate transformation parameters can be arbitrarily selected values. For example, all the coordinate transformation parameters can be set to 0 as the initial values.

The next process is to calculate the amount of mutual information of the fused image created using the second normalized 3D image, and the first normalized 3D image after the coordinate transformation (step S32). A value of this mutual information amount $I(A, B_{new})$ is calculated by Eqs (5)-(8) below.

[Mathematical Expression 5]

$$I(A, B_{new}) = H(A) + H(B_{new}) - H(A, B_{new}) \quad (5)$$

[Mathematical Expression 6]

$$H(A) = \sum \frac{N_{Ai}}{M_A} \log_2 \frac{N_{Ai}}{M_A} \quad (6)$$

[Mathematical Expression 7]

$$H(B_{new}) = \sum \frac{N_{Bi}}{M_B} \log_2 \frac{N_{Bi}}{M_B} \quad (7)$$

[Mathematical Expression 8]

$$H(A, B_{new}) = \sum \frac{N_{AiBi}}{M_{AB}} \log_2 \frac{N_{AiBi}}{M_{AB}} \quad (8)$$

Here $I(A, B_{new})$ is the mutual information amount, and $H(A)$, $H(B_{new})$, and $H(A, B_{new})$ are an entropy of the second normalized 3D image, an entropy of the first normalized 3D image after the coordinate transformation, and a joint entropy of the second normalized 3D image and the first normalized 3D image after the coordinate transformation, respectively. $N_{Ai}$ represents the number of voxels having pixel value $A_i$ in the second normalized 3D image, and $N_{Bi}$ the number of voxels having pixel value $B_i$ in the first normalized 3D image after the coordinate transformation. $N_{AiBi}$ represents the number of voxels where pixel values $A_i$ and $B_i$ exist simultaneously in the fused image. $M_A$, $M_B$, and $M_{AB}$ represent the number of voxels (matrix size) of the second normalized 3D image, the number of voxels (matrix size) of the first normalized 3D image after the coordinate transformation, and the number of voxels (matrix size) of the fused image, respectively.

In the fused image creation step, the calculation of mutual information amount is repeatedly executed while renewing the coordinate transformation parameters for the first normalized 3D image (step S34), and a condition to maximize the mutual information amount is extracted (step S33). Then a fused image is created from the first normalized 3D image subjected to the coordinate transformation with the coordinate transformation parameters to maximize the mutual information amount, and the second normalized 3D image (step S35).

The renewal and the optimization of the coordinate transformation parameters can be implemented using a variety of well-known algorithms. For example, it can be implemented by the direct search methods represented by the simplex method and the Powell method, or by the gradient methods (hill-climbing methods) represented by the steepest descent method (maximum grade method) and the conjugate gradient method (Tomoharu NAGAO, "Optimization Algorithms," first edition, SHOKODO Co., Ltd., 2000; Frederik Maes et al., IEEE Transactions on Medical Imaging, 1997, 16, 2, p. 187-198).

The steepest descent method will be described below as an example of the optimization algorithms. In the steepest descent method, first, the coordinate transformation of the first normalized 3D image is performed using arbitrary coordinate transformation parameters (Tx, Ty, Tz, $\theta x$, $\theta y$, $\theta z$), and a change rate is calculated between the mutual information amount calculated using the first normalized 3D image before the transformation and the mutual information amount calculated using the first normalized 3D image after the transformation. This calculation is repeated with various coordinate transformation parameters and a combination of transformation parameters to maximize the change rate of mutual information amount is extracted.

The next process is to calculate a change rate between the mutual information amount calculated using the first normalized 3D image after the transformation with the extracted coordinate transformation parameters and the mutual information amount calculated using the first normalized 3D image after the transformation with arbitrary coordinate transformation parameters different therefrom. The same operation as above is carried out to extract transformation parameters to maximize the change rate of mutual information amount and the first normalized 3D image is again transformed using them. This operation is repeatedly executed to converge the change rate of mutual information amount finally to 0. The condition for converging the change rate of mutual information amount to 0 corresponds to a transformation condition (coordinate transformation parameters) to maximize the mutual information amount. A fused image is created using the first normalized 3D image resulting from the transformation of position and orientation using this condition, and the second normalized 3D image.

Figure 5:
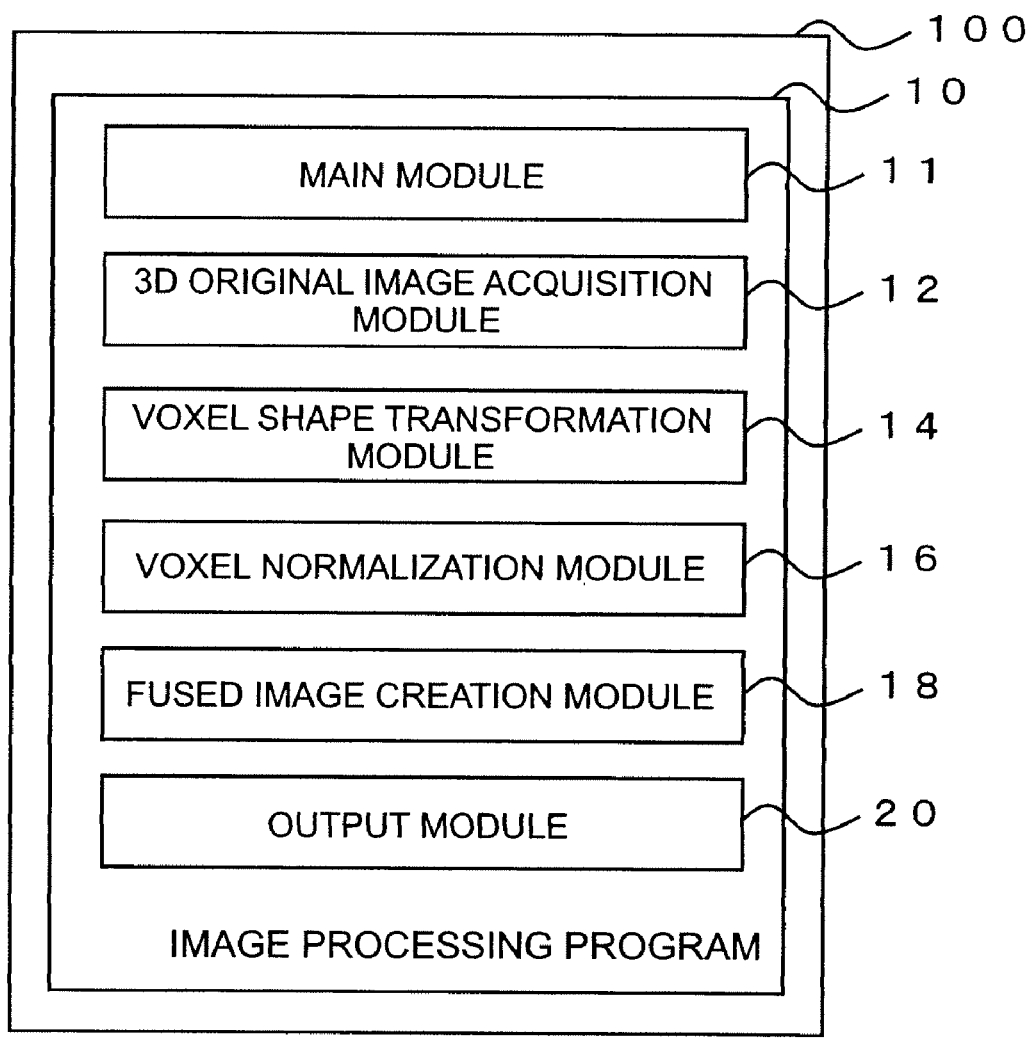
FIG. 5 is a drawing showing a configuration of an image processing program according to an embodiment of the present invention, together with a recording medium.

An image processing program according to an embodiment of the present invention will be described below. FIG. 5 is a drawing showing a configuration of the image processing program according to the embodiment of the present invention, together with a recording medium. The image processing program 10 shown in FIG. 5 is provided as stored in the recording medium 100. Examples of the recording medium 100 include recording media such as a flexible disk, CD-ROM, DVD, or ROM, semiconductor memories, and so on.

Figure 6:
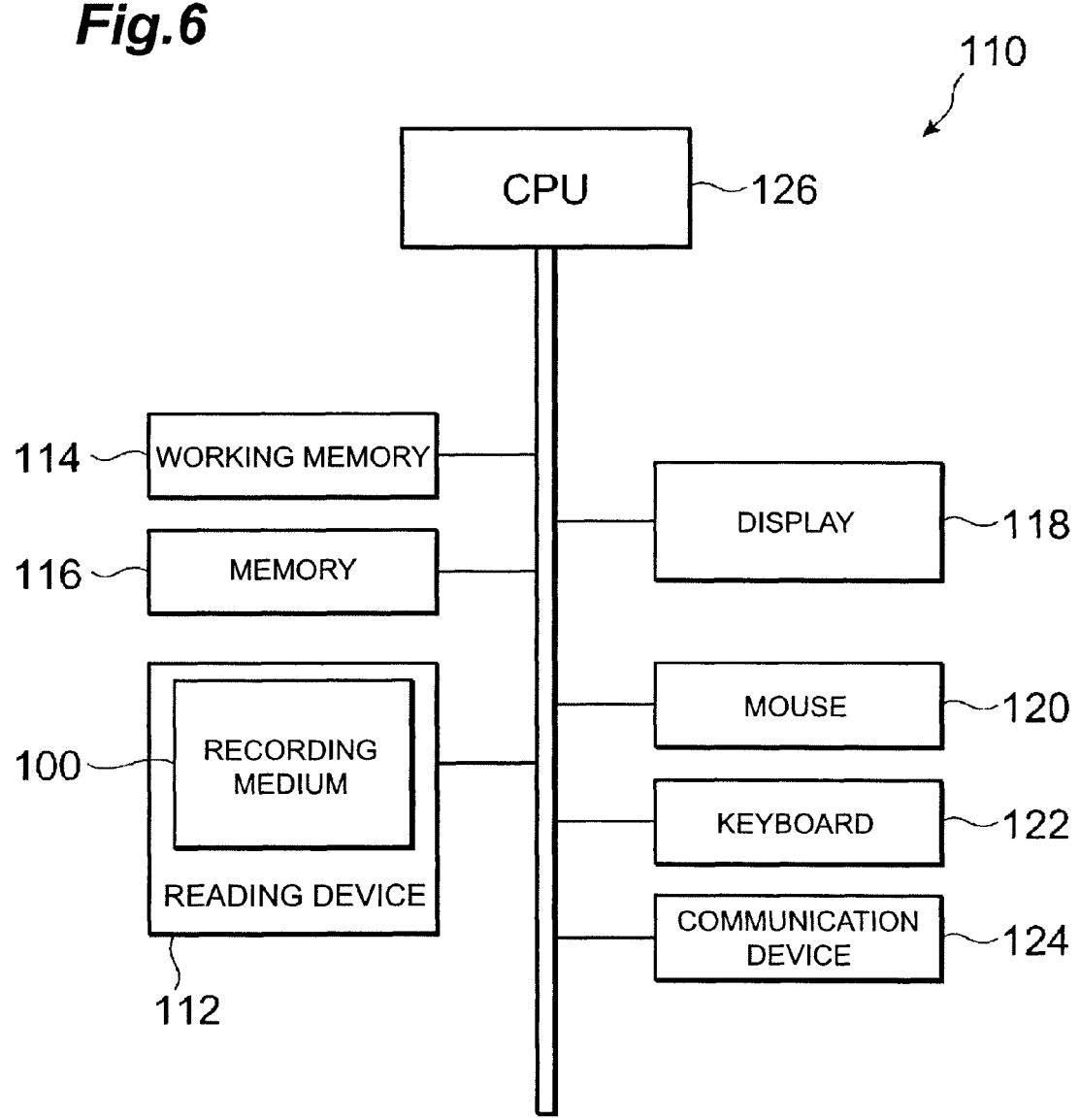
FIG. 6 is a drawing showing a hardware configuration of a computer for executing a program stored in a recording medium.
Figure 7:
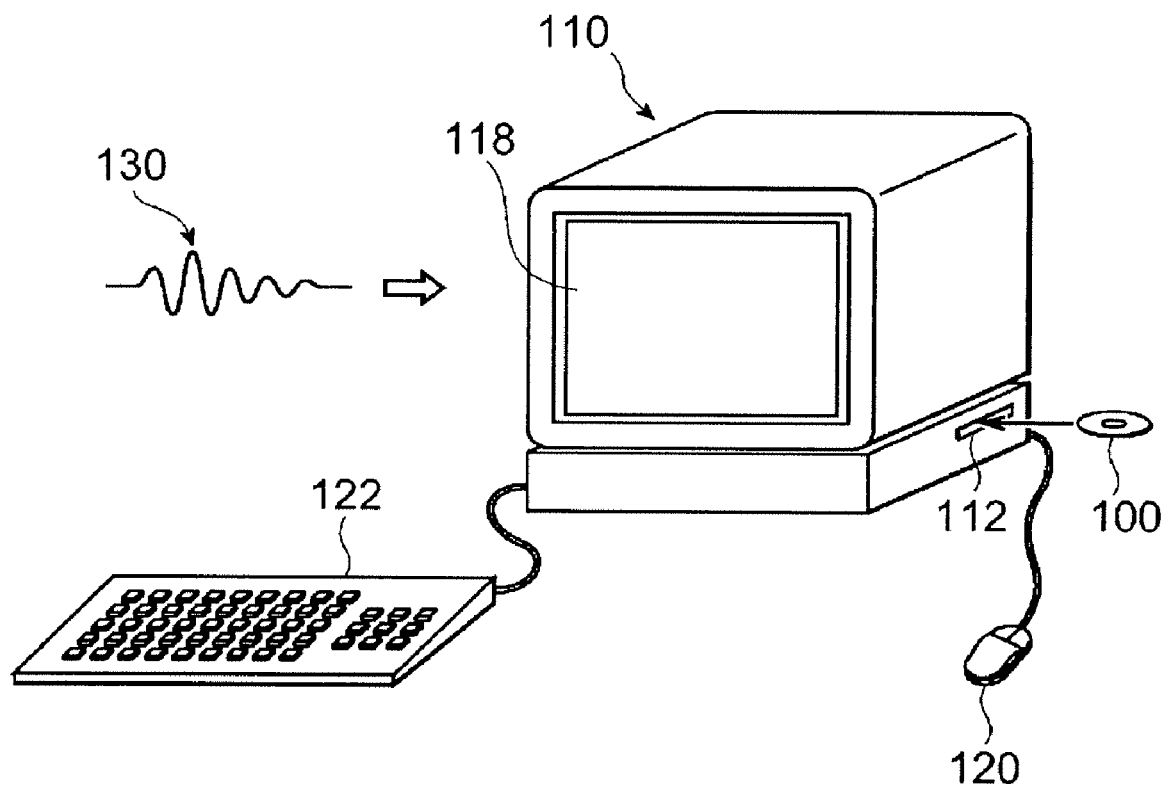
FIG. 7 is a perspective view of a computer for executing a program stored in a recording medium.

FIG. 6 is a drawing showing a hardware configuration of a computer for executing the program stored in the recording medium, and FIG. 7 a perspective view of the computer for executing the program stored in the recording medium. As shown in FIG. 6, the computer 110 has a reading device 112 such as a flexible disk drive unit, CD-ROM drive unit, or DVD drive unit, a working memory (RAM) 114 in which the operating system always remains, a memory 116 for storing the program stored in the recording medium 100, a display unit 118 such as a display, a mouse 120 and a keyboard 122 as input devices, a communication device 124 for transmission/reception of data and others, and a CPU 126 for controlling execution of the program. When the recording medium 100 is put into the reading device 112, the computer 110 becomes accessible to the image processing program 10 stored in the recording medium 100, through the reading device 112, and becomes ready to operate as the image processing apparatus of an embodiment of the present invention, based on the image processing program 10.

As shown in FIG. 7, the image processing program 10 may also be provided in the form of computer data signal 130 superimposed on a carrier wave, through a network. In this case, the computer 110 stores the image processing program 10 received by the communication device 124, into the memory 116 and then becomes able to execute the image processing program 10.

As shown in FIG. 5, the image processing program 10 has a main module 11 for generally controlling processing, a 3D original image acquisition module 12, a voxel shape transformation module 14, a voxel normalization module 16, a fused image creation module 18, and an output module 20.

The 3D original image acquisition module 12 lets the computer execute the aforementioned process of step S01, the voxel shape transformation module 14 lets the computer execute the aforementioned process of step S02, the voxel normalization module 16 lets the computer execute the aforementioned process of step S03, and the fused image creation module 18 lets the computer execute the aforementioned process of step S04. The output module 20 lets the display unit, such as a display, output the resulting fused image. In a preferred embodiment, the fused image is displayed while images of different sections are simultaneously displayed using a plurality of windows. In this case, a preferred display mode is to display a coronal image in one window and display axial images in the other windows, because this display mode better reflects the location information of involved part.

Figure 8:
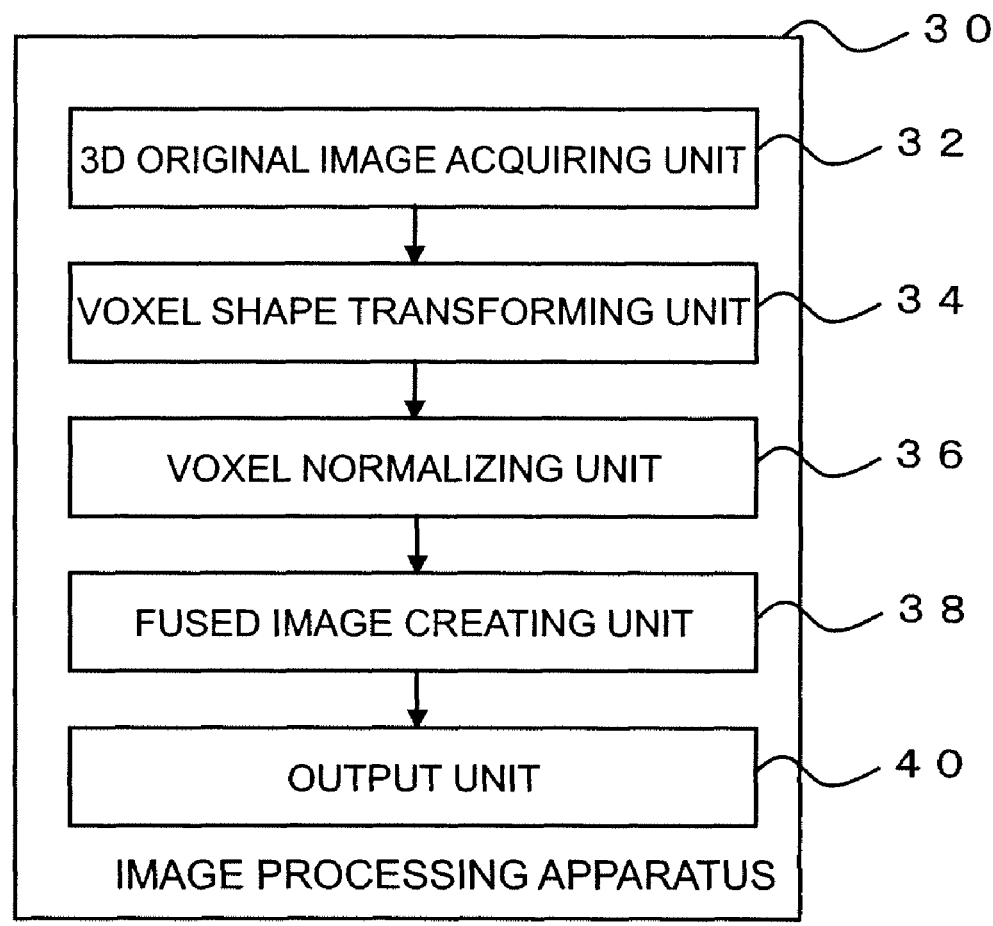
FIG. 8 is a drawing showing a configuration of an image processing apparatus according to an embodiment of the present invention.

An image processing apparatus according to an embodiment of the present invention will be described below. FIG. 8 is a drawing showing a configuration of the image processing apparatus of the embodiment of the present invention. The image processing apparatus 30 shown in FIG. 8 has the following functional components: 3D original image acquiring unit 32, voxel shape transforming unit 34, voxel normalizing unit 36, fused image creating unit 38, and output unit 40.

The 3D original image acquiring unit 32 is a part that executes the aforementioned process of step S01, the voxel shape transforming unit 34 is a part that executes the aforementioned process of step S02, the voxel normalizing unit 36 is a part that executes the aforementioned process of step S03, and the fused image creating unit 38 is a part that executes the aforementioned process of step S04. The output unit 40 is a part that outputs the resulting fused image to the display unit such as a display.

The image processing apparatus 30 of this configuration can be a computer which operates according to the aforementioned image processing program 10. The image processing apparatus 30 may also be a device composed of a dedicated circuit for executing the processes of the 3D original image acquiring unit 32, voxel shape transforming unit 34, voxel normalizing unit 36, fused image creating unit 38, and output unit 40.

EXAMPLES

The present invention will be described below in further detail on the basis of examples and comparative examples, but it is noted that the present invention is by no means intended to be limited to the examples below.

Comparative Example 1

Figure 9:
FIG. 9 is a drawing showing an example of head SPECT images.
Figure 10:
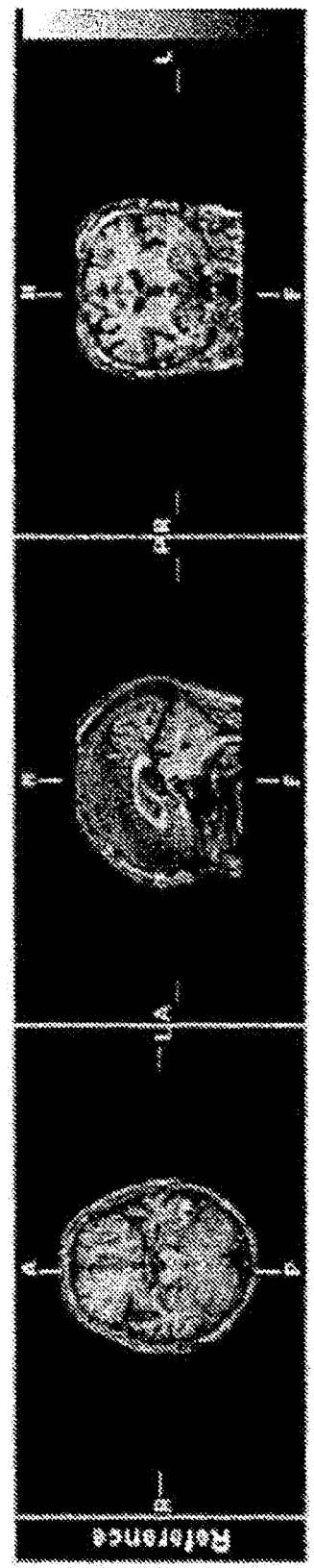
FIG. 10 is a drawing showing an example of head CT images in the same subject as in FIG. 9.

A fused image was created by the mutual information maximization method (Cost Function 5), using the first 3D original image of head FDG PET images (FIG. 9, matrix: 128×128, the number of slices: 14 slices, voxel size: 2.00 mm×2.00 mm×6.50 mm) and the second 3D original image of head MRI images (FIG. 10, matrix: 256×256, the number of slices: 99 slices, voxel size: 0.879 mm×0.879 mm×1.500 mm) and using the program of Corege.exe ver.5 mounted on NEUROSTAT (supplied by Prof. Satoshi Minoshima, School of Medicine in University of Washington). Namely, the fused image was created by the mutual information maximization method only, without the voxel shape transformation and the voxel normalization. The various set parameters in the program Corege.exe ver.5 were the following values.

Cost Function:=5
Cortical Threshold (%):=0.100000
Offset in Iteration (Phase 1):=20.000000
MI Bins:=16
Create Realigned image (0=no, 1=yes):=1
Create Subtraction image (0=no, 1=yes):=0
Normalization Mode (0-2):=0
Pixel Scaling Factor for binary output (0.0=normalized to max; 1.0=fixed; or exact):=1.000000
Pixel Value to Indicate Out of Field-of-View:=0.000000

Figure 11:
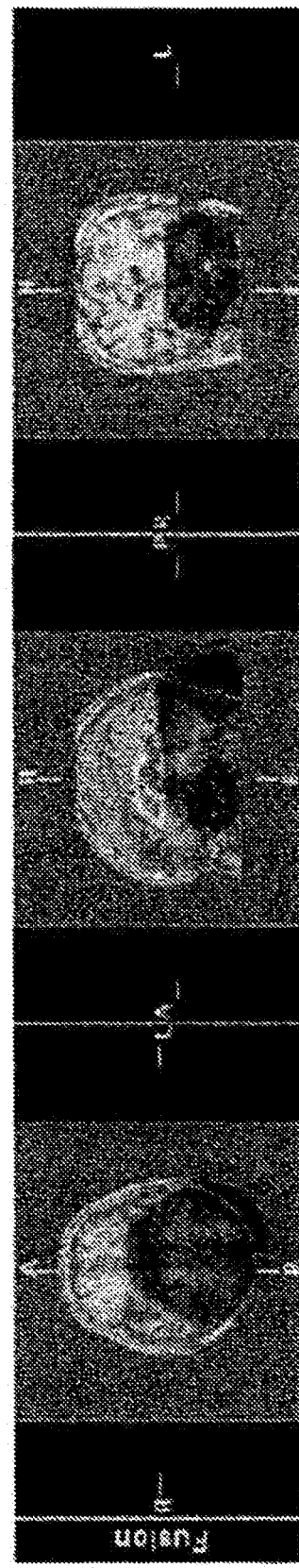
FIG. 11 is a drawing showing a fused image created by the mutual information maximization method only, using the images shown in FIG. 9 and FIG. 10.

The fused image thus created is shown in FIG. 11. In FIG. 11, images of plural sections in the fused image are displayed using a plurality of windows. As shown in FIG. 11, the overlapping accuracy in the created fused image is not always good, and in each section a pair of images was images overlapped with deviation from each other.

Example 1

A fused image was created in a manner described below, using the first 3D original image and the second 3D original image used in Comparative Example 1.

First, the interpolation process was conducted in the slice direction (or the z-axis direction) for the second 3D original image (MRI images), to implement the transformation into an image of matrix: 256×256, the number of slices: 167 slices, and voxel size: 0.879 mm×0.879 mm×0.879 mm, thereby obtaining a second 3D image. The first 3D original image was used as a first 3D image as it was.

Next, the interpolation process was conducted for axial images of the first 3D image (PET images), to implement the transformation into images of matrix: 256×256, and pixel size: 0.879 mm×0.879 mm. Then the interpolation process in the z-axis direction was conducted to implement the transformation into an image of matrix: 256×256, the number of slices: 167 slices, and voxel size: 0.879 mm×0.879 mm×0.879 mm, thereby obtaining a first normalized 3D image. The second 3D image was used as a second normalized 3D image as it was.

A fused image was created by the mutual information maximization method (Cost Function 5) using the first normalized 3D image and the second normalized 3D image and using the program Corege.exe ver.5 mounted on NEUROSTAT (supplied by Prof. Satoshi Minoshima, School of Medicine in University of Washington). The various set parameters in the program Corege.exe ver.5 were the same values as in Comparative Example 1.

Figure 12:
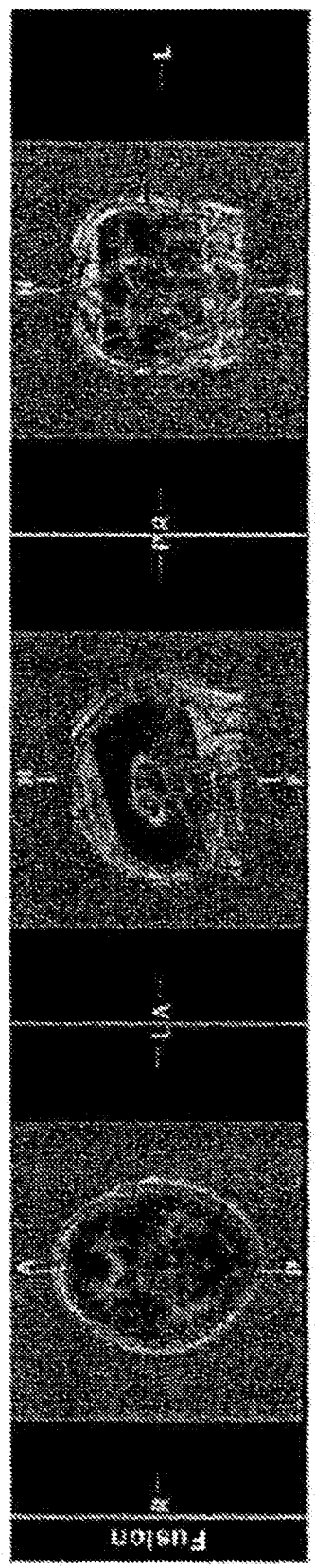
FIG. 12 is a drawing showing a fused image created by the image processing method according to the present invention, using the images shown in FIG. 9 and FIG. 10.

The fused image thus created is shown in FIG. 12. In FIG. 12, images of plural sections in the fused image are displayed using a plurality of windows. As shown in FIG. 12, the overlapping accuracy in the obtained fused image is good, and it was confirmed that the processing according to the present invention enabled the automatic creation of the good fused image.

Comparative Example 2

Figure 13:
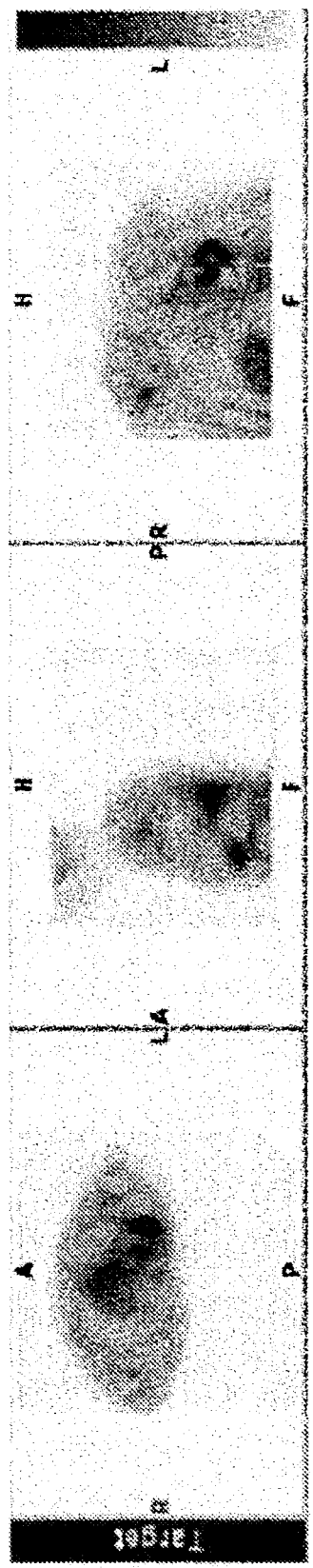
FIG. 13 is a drawing showing an example of chest SPECT images.
Figure 14:
FIG. 14 is a drawing showing an example of chest MRI images in the same subject as in FIG. 13.

A fused image was created by the mutual information maximization method (Cost Function 5), using the first 3D original image of chest FDG PET images (FIG. 13, matrix: 128×128, the number of slices: 136 slices, voxel size: 4.29 mm×4.29 mm×4.29 mm) and the second 3D original image of chest CT images (FIG. 14, matrix: 256×256, the number of slices: 81 slices, voxel size: 1.875 mm×1.875 mm×5.000 mm) and using the program Corege.exe ver.5 mounted on NEUROSTAT (supplied by Prof. Satoshi Minoshima, School of Medicine in University of Washington). Namely, the fused image was created by the mutual information maximization method only, without the voxel shape transformation and the voxel normalization. The various set parameters in the program Corege.exe ver.5 were the same values as in Comparative Example 1.

Figure 15:
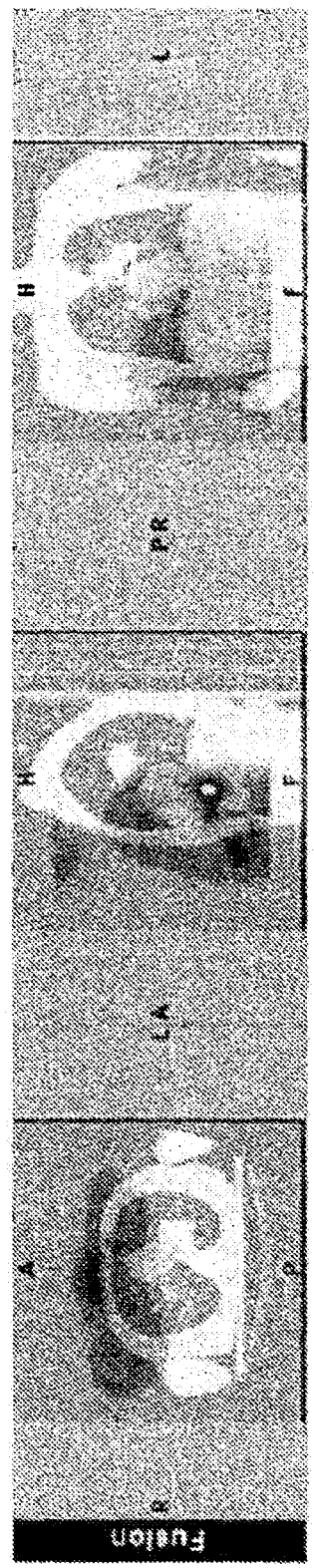
FIG. 15 is a drawing showing a fused image created by the mutual information maximization method only, using the images shown in FIG. 13 and FIG. 14.

The fused image thus created is shown in FIG. 15. In FIG. 15, images of plural sections in the fused image are displayed using a plurality of windows. As shown in FIG. 15, the overlapping accuracy in the created fused image is not always good, and in each section a pair of images was images overlapped with deviation from each other.

Example 2

A fused image was created in a manner described below, using the first 3D original image and the second 3D original image used in Comparative Example 2.

First, the interpolation process was conducted in the slice direction (or the z-axis direction) for the second 3D original image (CT images), to implement the transformation into an image of matrix: 256×256, the number of slices: 312 slices, and voxel size: 1.875 mm×1.875 mm×1.875 mm, thereby obtaining a second 3D image. The first 3D original image was used as a first 3D image as it was.

Next, the interpolation process was conducted for axial images of the first 3D image (PET images), to implement the transformation into images of matrix: 256×256 and pixel size: 1.875 mm×1.875 mm. Then the interpolation process in the z-axis direction was conducted to implement the transformation into an image of matrix: 256×256, the number of slices: 312 slices, and voxel size: 1.875 mm×1.875 mm×1.875 mm, thereby obtaining a first normalized 3D image. The second 3D image was used as a second normalized 3D image as it was.

A fused image was created by the mutual information maximization method (Cost Function 5), using the first normalized 3D image and the second normalized 3D image and using the program Corege.exe ver.5 mounted on NEUROSTAT (supplied by Prof. Satoshi Minoshima, School of Medicine in University of Washington). The various set parameters in the program Corege.exe ver.5 were the same values as in Comparative Example 1.

Figure 16:
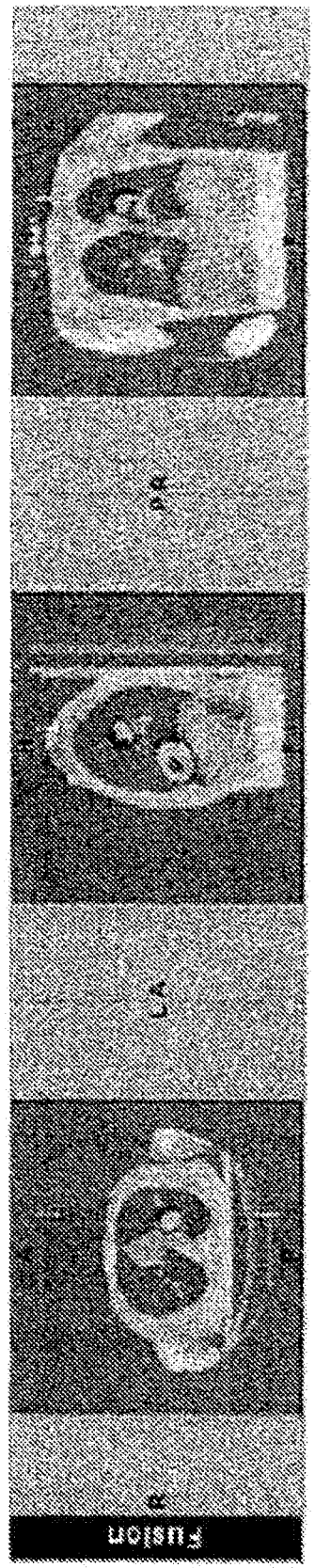
FIG. 16 is a drawing showing a fused image created by the image processing method according to the present invention, using the images shown in FIG. 13 and FIG. 14.

The fused image thus created is shown in FIG. 16. In FIG. 16, images of plural sections in the fused image are displayed using a plurality of windows. As shown in FIG. 16, the overlapping accuracy in the obtained fused image is good, and it was confirmed that the processing according to the present invention enabled the automatic creation of the good fused image, with the good overlapping accuracy in the resultant fused image.

INDUSTRIAL APPLICABILITY

The present invention is useful for automatic and accurate creation of the fused image and applicable in the field of diagnostic imaging apparatus.

The invention claimed is:

1. An image processing method comprising:
    a voxel normalization step further comprising equalizing voxel sizes of a first 3D image created from a plurality of first tomographic images obtained from an arbitrary part of a subject and a second 3D image created from a plurality of second tomographic images obtained from said part by applying a pixel interpolation process to at least one of the first and the second 3D images, and assigning voxels each having a NULL code to regions other than an effective field of view of one of the first and the second 3D images which have a smaller effective field of view than the other, thereby creating a first normalized 3D image corresponding to the first 3D image and a second normalized 3D image corresponding to the second 3D image both having the same size of voxels and the same effective field of view; and
    a fused image creation step of creating a fused image, using the first normalized 3D image and the second normalized 3D image.

2. The image processing method according to claim 1, wherein the pixel interpolation process is performed by a linear interpolation method.

3. The image processing method according to claim 1, further comprising a voxel shape transformation step further comprising at least one of transforming each voxel in a first 3D original image consisting of the plurality of first tomographic images to a voxel of a cubic shape for creating the first 3D image, and transforming each voxel in a second 3D original image consisting of the plurality of second tomographic images to a voxel of a cubic shape for creating the second 3D image.

4. The image processing method according to claim 3, wherein the voxel shape transformation step comprises creating the first 3D image or the second 3D image by a linear interpolation method.

5. The image processing method according to claim 1, wherein the fused image creation step comprises creating the fused image by the mutual information maximization method.

6. A computer readable medium encoded with an image processing program for causing a computer to execute the following steps:
a voxel normalization step comprising equalizing voxel sizes of a first 3D image created from a plurality of first tomographic images obtained from an arbitrary part of a subject and a second 3D image created from a plurality of second tomographic images obtained from said part by applying a pixel interpolation process to at least one of the first and the second 3D images, and assigning voxels each having a NULL code to regions other than an effective field of view of one of the first and the second 3D images which have a smaller effective field of view than the other, thereby creating a first normalized 3D image corresponding to the first 3D image and a second normalized 3D image corresponding to the second 3D image both having the same size of voxels and the same number of voxels; and
a fused image creation step of creating a fused image, using the first normalized 3D image and the second normalized 3D image.

7. The computer readable medium according to claim 6, wherein the pixel interpolation process is performed by a linear interpolation method.

8. The computer readable medium according to claim 6, wherein the image processing program causes the computer to further execute the following step:
a voxel shape transformation step further comprising at least one of transforming each voxel in a first 3D original image consisting of the plurality of first tomographic images to a voxel of a cubic shape for creating the first 3D image, and transforming each voxel in a second 3D original image consisting of the plurality of second tomographic images to a voxel of a cubic shape for creating the second 3D image.

9. The computer readable medium according to claim 8, wherein in the voxel shape transformation step the computer is made to create the first 3D image or the second 3D image by a linear interpolation method.

10. The computer readable medium according to claim 6, wherein in the fused image creation step the computer is made to create the fused image by the mutual information maximization method.

11. An image processing apparatus comprising:
voxel normalizing means for equalizing voxel sizes of a first 3D image created from a plurality of first tomographic images obtained from an arbitrary part of a subject and a second 3D image created from a plurality of second tomographic images obtained from said part by applying a pixel interpolation process to at least one of the first and the second 3D images, and assigning voxels each having a NULL code to regions other than an effective field of view of one of the first and the second 3D images which have a smaller effective field of view than the other, thereby creating a first normalized 3D image corresponding to the first 3D image and a second normalized 3D image corresponding to the second 3D image both having the same size of voxels and the same effective field of view; and
fused image creating means for creating a fused image, using the first normalized 3D image and the second normalized 3D image.

12. The image processing apparatus according to claim 11, wherein the pixel interpolation process is performed by a linear interpolation method.

13. The image processing apparatus according to claim 11, further comprising voxel shape transforming means configured to perform at least one of transforming each voxel in a first 3D original image consisting of the plurality of first tomographic images to a voxel of a cubic shape for creating the first 3D image, and transforming each voxel in a second 3D original image consisting of the plurality of second tomographic images to a voxel of a cubic shape for creating the second 3D image.

14. The image processing apparatus according to claim 13, wherein the voxel shape transforming means creates the first 3D image or the second 3D image by a linear interpolation method.

15. The image processing apparatus according to claim 11, wherein the fused image creating means creates the fused image by the mutual information maximization method.

* * * * *

UNITED STATES PATENT AND TRADEMARK OFFICE
CERTIFICATE OF CORRECTION

PATENT NO.      : 8,126,243 B2  
APPLICATION NO. : 12/064430  
DATED           : February 28, 2012  
INVENTOR(S)     : Kazuo Hamada et al.

Page 1 of 1

It is certified that error appears in the above-identified patent and that said Letters Patent is hereby corrected as shown below:

Title Page  
Item (22), PCT Filed:  
Delete "Feb. 21, 2006" and replace with --August 17, 2006--.

Signed and Sealed this  
Thirtieth Day of April, 2013

Teresa Stanek Rea  
*Acting Director of the United States Patent and Trademark Office*